United States Patent
Yan et al.

(10) Patent No.: US 8,237,923 B2
(45) Date of Patent: Aug. 7, 2012

(54) BIO-SAMPLE IMAGE PICKUP DEVICE

(75) Inventors: Shuo-Ting Yan, Hsinchu (TW); Sy-Haw Wang, Hsinchu (TW); Wei-Li Hong, Hsinchu (TW)

(73) Assignee: Yayatech Co., Ltd., Hsinchu (TW)

( * ) Notice: Subject to any disclaimer, the term of this patent is extended or adjusted under 35 U.S.C. 154(b) by 114 days.

(21) Appl. No.: 12/834,424

(22) Filed: Jul. 12, 2010

(65) Prior Publication Data

US 2011/0255084 A1  Oct. 20, 2011

(30) Foreign Application Priority Data

Apr. 15, 2010  (TW) ................ 99111799 A

(51) Int. Cl.
*G01N 21/01* (2006.01)
*G01N 1/10* (2006.01)

(52) U.S. Cl. .................. 356/246; 356/244; 356/317

(58) Field of Classification Search .......... 356/246, 356/244, 432–444, 417; 250/458.1, 461.1
See application file for complete search history.

(56) References Cited

U.S. PATENT DOCUMENTS

| | | | | |
|---|---|---|---|---|
| 4,522,204 A * | 6/1985 | Kurahashi et al. | ............ | 600/532 |
| 4,580,895 A * | 4/1986 | Patel | ................................ | 356/39 |
| 4,758,730 A * | 7/1988 | Bazin et al. | ............... | 250/559.22 |
| 4,810,096 A * | 3/1989 | Russell et al. | ................ | 356/436 |
| 5,459,325 A * | 10/1995 | Hueton et al. | ............. | 250/458.1 |
| 5,528,045 A * | 6/1996 | Hoffman et al. | ........... | 250/458.1 |
| 6,271,042 B1 * | 8/2001 | Watson et al. | ................ | 436/172 |
| 6,320,660 B1 * | 11/2001 | Ju et al. | .......................... | 356/417 |
| 6,388,751 B1 * | 5/2002 | Holley | ........................... | 356/436 |
| 6,727,987 B2 * | 4/2004 | Yonezawa | ................... | 356/237.2 |
| 7,355,698 B2 * | 4/2008 | Shah et al. | ..................... | 356/246 |
| 7,508,516 B2 * | 3/2009 | Sugiyama et al. | ............. | 356/417 |

* cited by examiner

*Primary Examiner* — Sang Nguyen
(74) *Attorney, Agent, or Firm* — Muncy, Geissler, Olds & Lowe, PLLC

(57) ABSTRACT

A bio-sample image pickup device includes a light source module, a carrier, an image pickup unit, a first filter set, and a second filter set. The carrier carries the light source module and the bio-sample, and moves between a first position and a second position. The first filter set between the light source module and the image pickup unit for filtering the light emitted by the light source module, and the image pickup unit picks up the image of the bio-sample through the first filter set in the first position. The second filter set in the second position filters the light emitted by the light source module for allowing an operator to see the bio-sample in the second position through the second filter.

10 Claims, 8 Drawing Sheets

BIO-SAMPLE IMAGE PICKUP DEVICE

BACKGROUND OF THE INVENTION

1. Technical Field

The present invention relates to a bio-sample image pickup device, which allows the operator to pick up the image of a bio-sample and also to view the bio-sample directly.

2. Description of the Prior Art

Please refer to FIG. 1. A conventional bio-sample image pickup device 10 is shown comprising a light source module 11, a filter 13 and an image pickup unit 15. The filter 13 is disposed between the light source module 11 and the image pickup unit 15. When in use, a bio-sample 12 is placed on the light source module 11, and the image pickup unit 15 is operated to pick up the image of the bio-sample 12 through the filter 13. The bio-sample 12 can be, for example, a DNA gel obtained through gel electrophoresis.

In actual practice, the light source module 11 can be a light box adapted to emit light L that can be blue light. The bio-sample 12 can be placed on the top side of the light source module 11 so that the emitted light L can project onto the bio-sample 12. At this time, a part of the emitted light L goes through the bio-sample 12, and the other part of the emitted light L excites the bio-sample 12 to produce a first light L1.

The filter 13 is an amber filter adapted for filtering the light L that passes through the bio-sample 12. The light L can be blue light. The wavelength of the first light L1 is greater than the light L. The filter 12 filter the light L (blue light) and allow the first light L1 to pass therethrough and to project onto the image pickup unit 15 so that the image pickup unit 15 can pick up the image of the first light L1.

The aforesaid bio-sample image pickup device 10 can pick up the image of a bio-sample 12. However, it still has drawbacks. For example, when using the bio-sample image pickup device 10 to pick up the image of a bio-sample 12, the operator may need to perform a follow-up test and analysis on a particular area of the bio-sample 12. At this time, the operator needs to remove the bio-sample 12 from the bio-sample image pickup device 10 and then place the bio-sample 12 on another light source module. Further, the operator must wear a pair of amber eyeglasses so as to see the image of the bio-sample 12 and then to cut off a part of the bio-sample 12 for test and analysis.

SUMMARY OF THE PRESENT INVENTION

It is, therefore, the main object of the present invention to provide a bio-sample image pickup device, which enables the operator to pick up the image of a bio-sample through an image pickup unit and to observe the bio-sample on a light source module through a filter.

It is another object of the present invention to provide a bio-sample image pickup device, which has a light source module mounted on a carrier for movement between a first position and a second position so that when the light source module is in the first position, a bio-sample image pickup device can be operated to pick up the image of the bio-sample; when the light source module is in the second position, the operator can see the image of the bio-sample and cut off a part of the bio-sample.

It is still another object of the present invention to provide a bio-sample image pickup device, which has a first filter disposed in the first position and a second filter disposed in the second position so that the image pickup unit can pick up the image of a bio-sample in the first position, and the operator can see the image of the bio-sample in the second position through the second filter.

It is still another object of the present invention to provide a bio-sample image pickup device, which has a filter disposed on the light source module. A bio-sample placed between the filter and the light source module can move with the light source module between a first position and a second position, so that when the light source module is moved to carry the bio-sample and the filter to the first position, the image pickup unit can be operated to pick up the image of the bio-sample through the filter; when the light source module is moved to carry the bio-sample and the filter to the second position, the operator can see the image of the bio-sample in the second position through the filter.

It is still another object of the present invention to provide a bio-sample image pickup device, which uses one single filter that extends from a first position to a second position with a part thereof disposed between an image pickup unit and a light source module so that the image pickup unit can be operated to pick up the image of a bio-sample in the first position through the filter, and the operator can see the image of the bio-sample and cut off a part of the bio-sample in the second position through the filter.

To achieve these and other objects of the present invention, a bio-sample image pickup device comprises a light source module adapted to emit light, allowing the emitted light to be projected onto a bio-sample, a carrier adapted to carry the light source module, allowing the light source module to be moved between a first position and a second position, an image pickup unit adapted to pick up the image of the bio-sample in the first position, a first filter set between the light source module and the image pickup unit and adapted to filter the light emitted by the light source module, and a second filter set in the second position and adapted to filter the light emitted by the light source module, allowing an operator to see the image of the bio-sample in the second position through the second filter.

To achieve these and other objects of the present invention, a bio-sample image pickup device comprises a light source module adapted to emit light, allowing the emitted light to be projected onto a bio-sample, a carrier adapted to carry the light source module, allowing the light source module to be moved between a first position and a second position, an image pickup unit adapted to pick up the image of the bio-sample in the first position, and a filter mounted on the light source module and movable with the light source module and adapted to filter the light emitted by the light source module.

To achieve these and other objects of the present invention, a bio-sample image pickup device comprises a light source module adapted to emit light, allowing the emitted light to be projected onto a bio-sample, a carrier adapted to carry the light source module, allowing the light source module to be moved between a first position and a second position, an image pickup unit adapted to pick up the image of the bio-sample in the first position, and a filter extending from the first position to the second position and adapted to filter the light emitted by the light source module and having a part thereof disposed between the light source module and the image pickup unit.

DETAILED DESCRIPTION OF THE PREFERRED EMBODIMENTS

Figure 1:
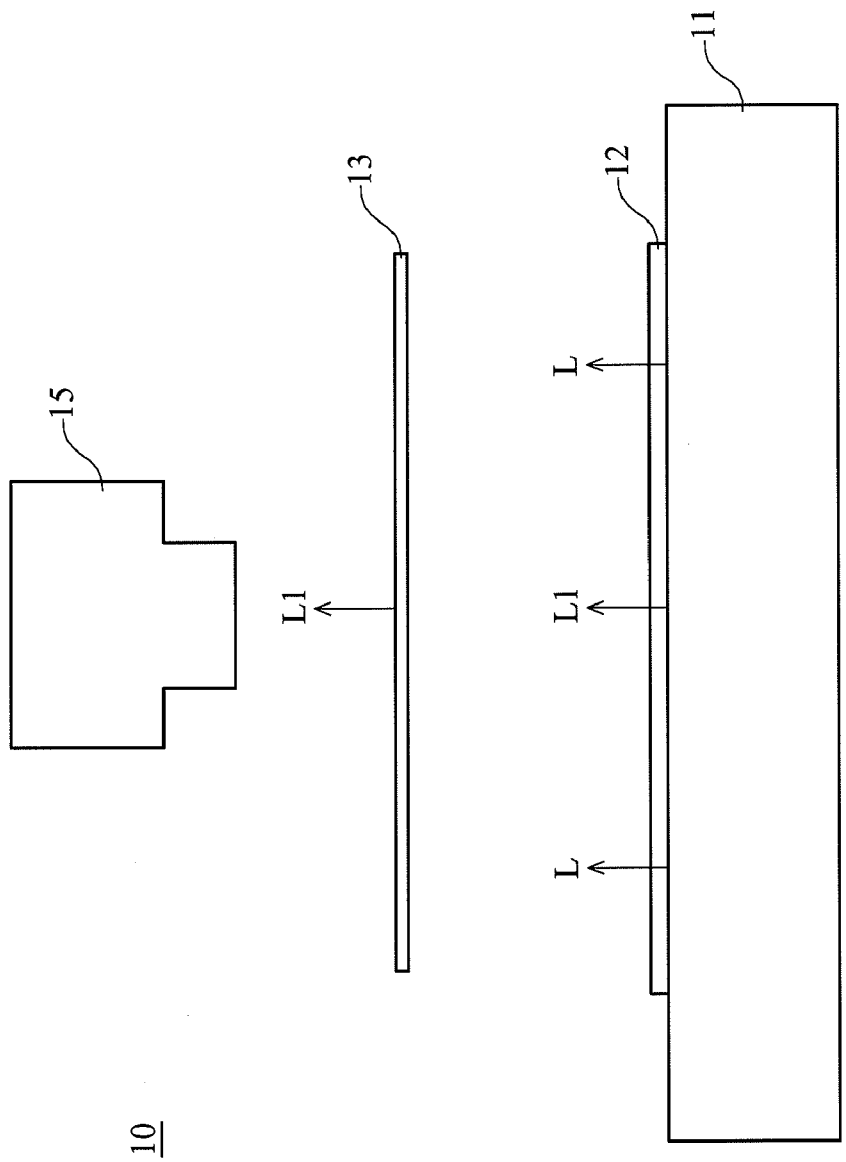
FIG. 1 is a schematic drawing showing the structure of a bio-sample image pickup device according to the prior art.
Figure 2A:
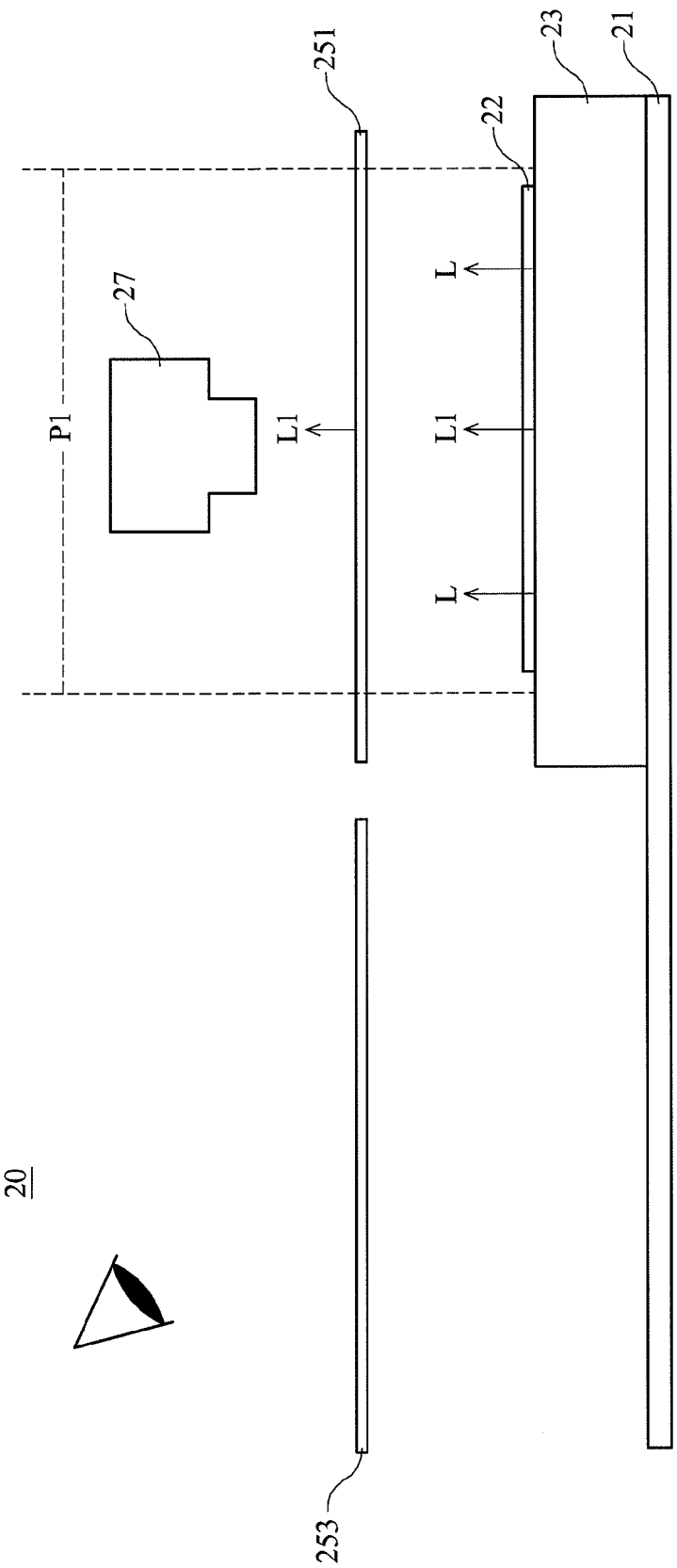
FIG. 2A is a schematic drawing showing the structure of a bio-sample image pickup device in accordance with a first embodiment of the present invention.
Figure 2B:
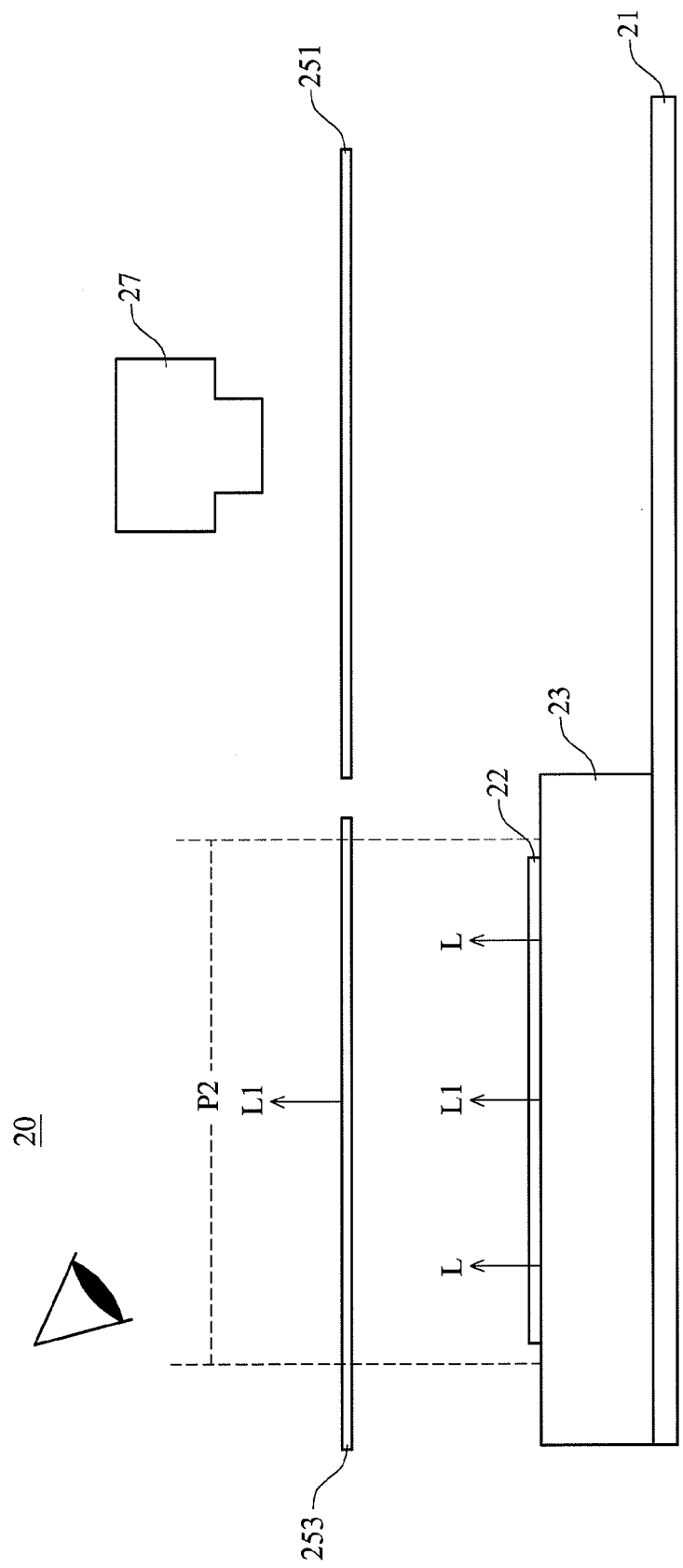
FIG. 2B corresponds to FIG. 2A, showing the bio-sample and the light source module moved to the second position.

Referring to FIG. 2A and FIG. 2B, a bio-sample image pickup device 20 in accordance with a first embodiment of the present invention is shown comprising a carrier 21, a light source module 23, a first filter 251, a second filter 253 and an image pickup unit 27. When in use, a bio-sample 22 is placed on the light source module 23, allowing the image of the bio-sample 22 to be picked up by the image pickup unit 27.

The light source module 23 is adapted for emitting light L. The light source module 23 can be a light box. When in use, the bio-sample 22 is placed on the top side of the light source module 23, allowing the emitted light L to be projected onto the bio-sample 22. At this time, a part of the emitted light L excites the bio-sample 22 to produce a different wavelength of first light L1. For example, the bio-sample 22 can be a DNA gel obtained through gel electrophoresis, and the emitted light L excites the bio-sample 22 to produce fluorescence (first light L1).

The carrier 21 is adapted for carrying the light source module 23, allowing the light source module 23 to be moved thereon. The bio-sample image pickup device 20 defines a first position P1 and a second position P2. The light source module 23 is movable between the first position P1 and the second position P2. The first position P1 can be defined as an image pickup zone. The second position P2 can be defined as an operation zone. According to this first embodiment, the carrier 21 is a sliding track. The light source module 23 is slidably mounted on the sliding track (carrier 21), and movable along the sliding track (carrier 21) between the first position P1 and the second position P2.

The first filter 251 and the second filter 253 can be identical, and adapted for filtering the light L emitted by the light source module 23, allowing the first light L1 to pass therethrough. The first filter 251 is positioned in the first position P1. The second filter 253 is positioned in the second position. When the light source module 23 and the bio-sample 22 are in the first position P1, the first filter 251 is disposed above the light source module 23 and the bio-sample 22. When the light source module 23 and the bio-sample 22 are in the second position P2, the second filter 253 is disposed above the light source module 23 and the bio-sample 22.

Further, the emitted light L can be blue light or ultraviolet light. The wavelength of the first light L1 is greater than the emitted light L. The first filter 251 and the second filter 253 are amber filters adapted for filtering blue light or ultraviolet light (the emitted light L).

The image pickup unit 27 is disposed above the first filter 251. When the light source module 23 and the bio-sample 22 are in the first position P1, the first filter 251 is disposed between the light source module 23 and the image pickup unit 27 for filtering the emitted light L that passes through the bio-sample 22, allowing the excited first light L1 to pass through the first filter 251 and to be mapped onto the image pickup unit 27 so that the image formed of the first light L1 can pick up the image of the bio-sample 22, as shown in FIG. 2A.

When the light source module 23 and the bio-sample 22 are in the second position P2, the operator can see the image of the bio-sample 22 through the second filter 253 and cut off a part of the bio-sample 22. The second filter 253 in the second position P2 will filter the emitted light L, allowing the first light L1 to pass therethrough, thus, the operator can see the image of the bio-sample 22 that is formed of the first light L1 and directly cut off a part of the bio-sample 22 in the second position P2, as shown in FIG. 2B.

Figure 3:
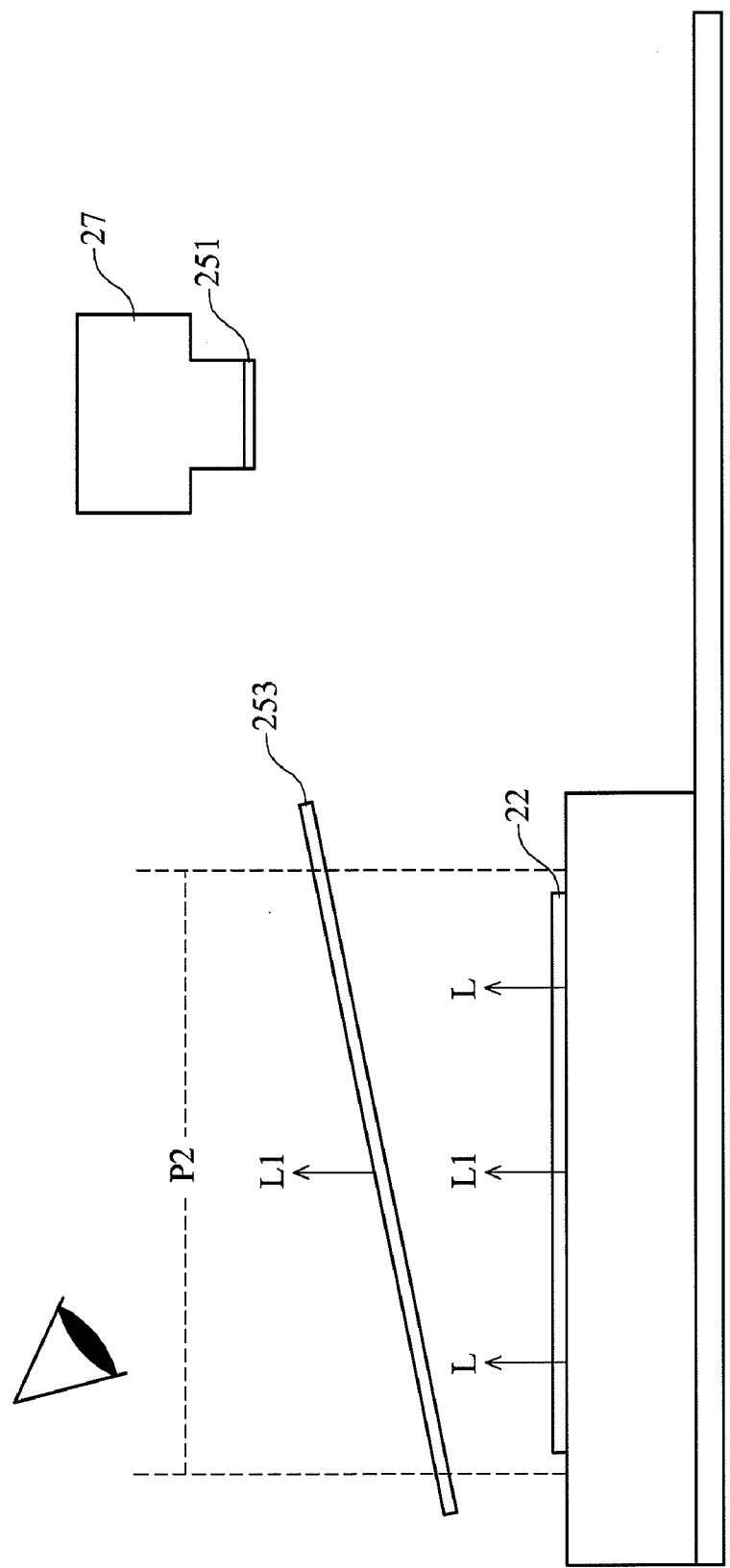
FIG. 3 is a schematic drawing of the first embodiment of the present invention, showing the first filter mounted on the image pickup unit and the second filter obliquely disposed in an oblique manner.

Further, the first filter 251 can be directly mounted on the image pickup unit 27. For example, the first filter 251 can be mounted on the lens of the image pickup unit 27. In this case, the first filter 251 filters the emitted light L, allowing the image pickup unit 27 to pick up the image of the bio-sample 22 that is formed of the first light L1. Further, the second filter 253 can be set obliquely, or arranged for allowing adjustment of its angular position, facilitating the operator to view the bio-sample 22 through the second filter 253 or to cut off a part of the bio-sample 22, as shown in FIG. 3.

Figure 4A:
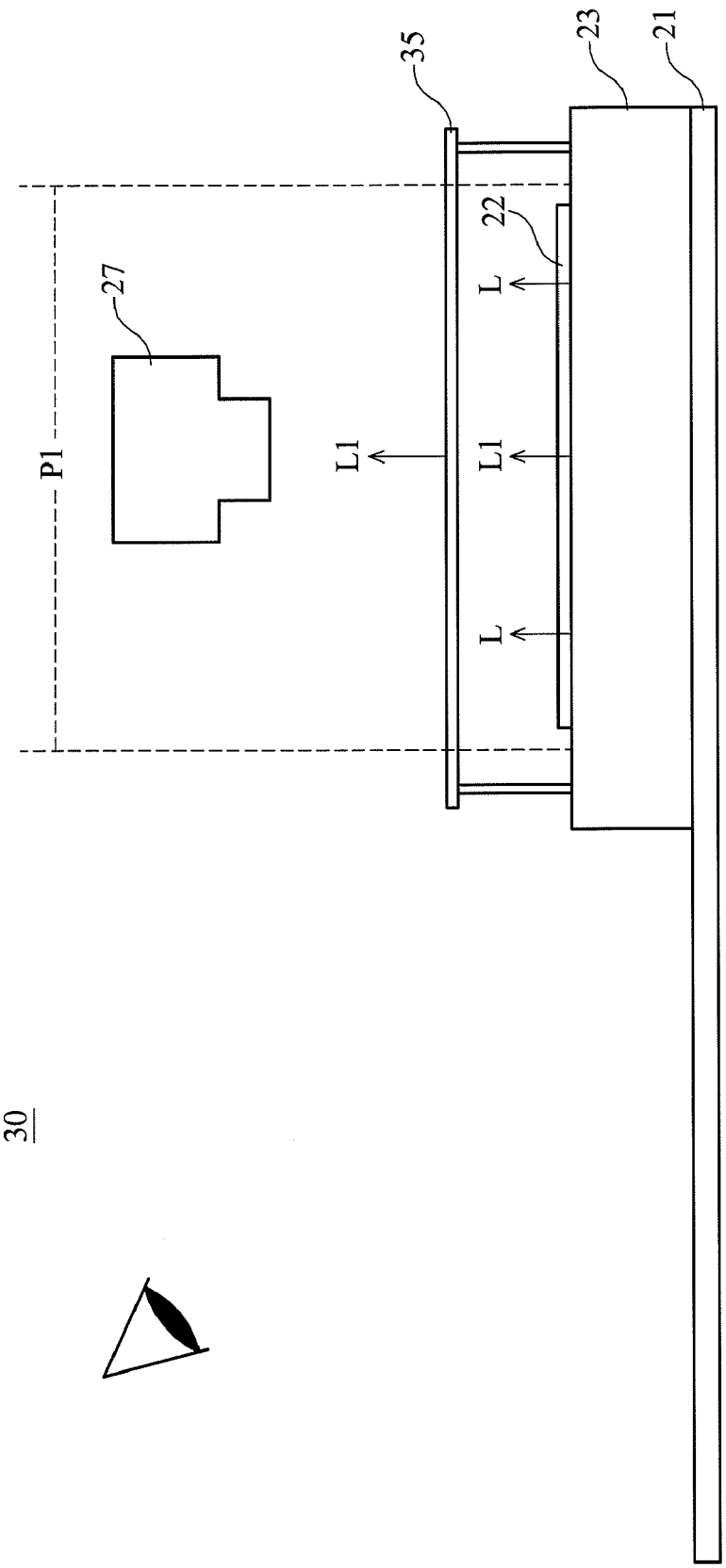
FIG. 4A is a schematic drawing showing the structure of a bio-sample image pickup device in accordance with a second embodiment of the present invention.
Figure 4B:
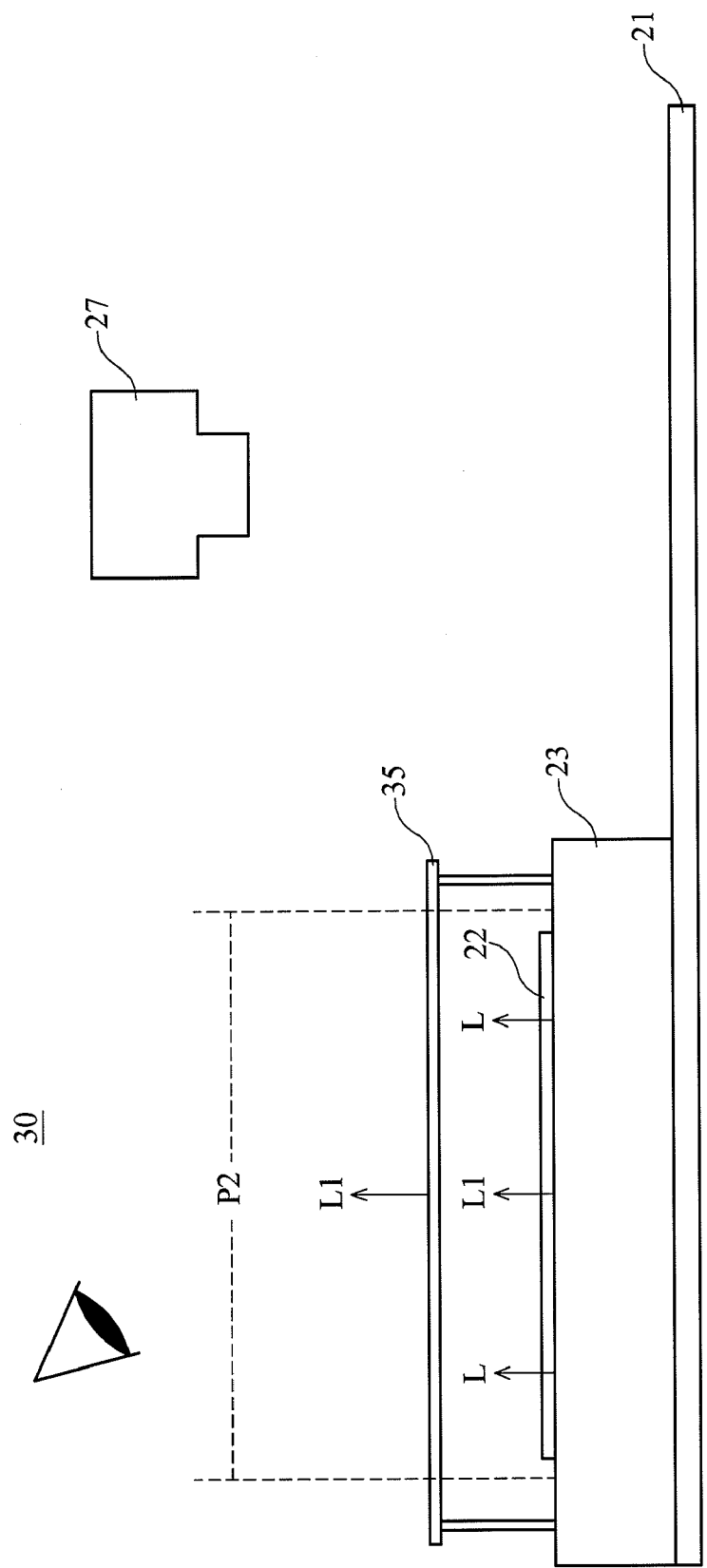
FIG. 4B corresponds to FIG. 4A, showing the filter, the bio-sample and the light source module moved to the second position.

FIG. 4A and FIG. 4B show a bio-sample image pickup device 30 in accordance with a second embodiment of the present invention. According to this second embodiment, the bio-sample image pickup device 30 comprises a carrier 21, a light source module 23, a filter 35 and an image pickup unit 27. When in use, a bio-sample 22 is placed on the light source module 23, allowing the image of the bio-sample 22 to be picked up by the image pickup unit 27.

The filter 35 is mounted on the light source module 21. When the light source module 23 is moved on the carrier 21, the filter 35 is moved with the light source module 23. According to this second embodiment, the filter 35 and the light source module 23 are movable on the carrier 21 between a first position P1 and a second position P2.

When in use, the bio-sample 22 is placed in between the filter 35 and the light source module 23. When the light source module 23 and the bio-sample 22 are in the first position P1, a part of the emitted light L goes through the bio-sample 22, the other part of the emitted light L excites the bio-sample 22 to produce a first light L1. The filter 35 above the light source module 23 filters the emitted light L, allowing the first light L1 to pass therethrough toward the image pickup unit 27 so that the image pickup unit 27 can pick up the image of the bio-sample 22, as shown in FIG. 4A.

When the light source module 23, filter 35 and the bio-sample 22 are in the second position P2, the operator can see the image of the bio-sample 22 through the filter 35 and cut off or a part of the bio-sample 22, as shown in FIG. 4B.

According to this second embodiment, the filter 35 is movable with the light source module 23. Therefore, the image pickup device 30 requires only one single filter 35 to filter the emitted light L in the first position P1 and the second position P2, allowing the image pickup unit 27 to pick up the image of the bio-sample 22 in the first position P1 and the operator to see the image of the bio-sample 22 in the second position P2.

Figure 5A:
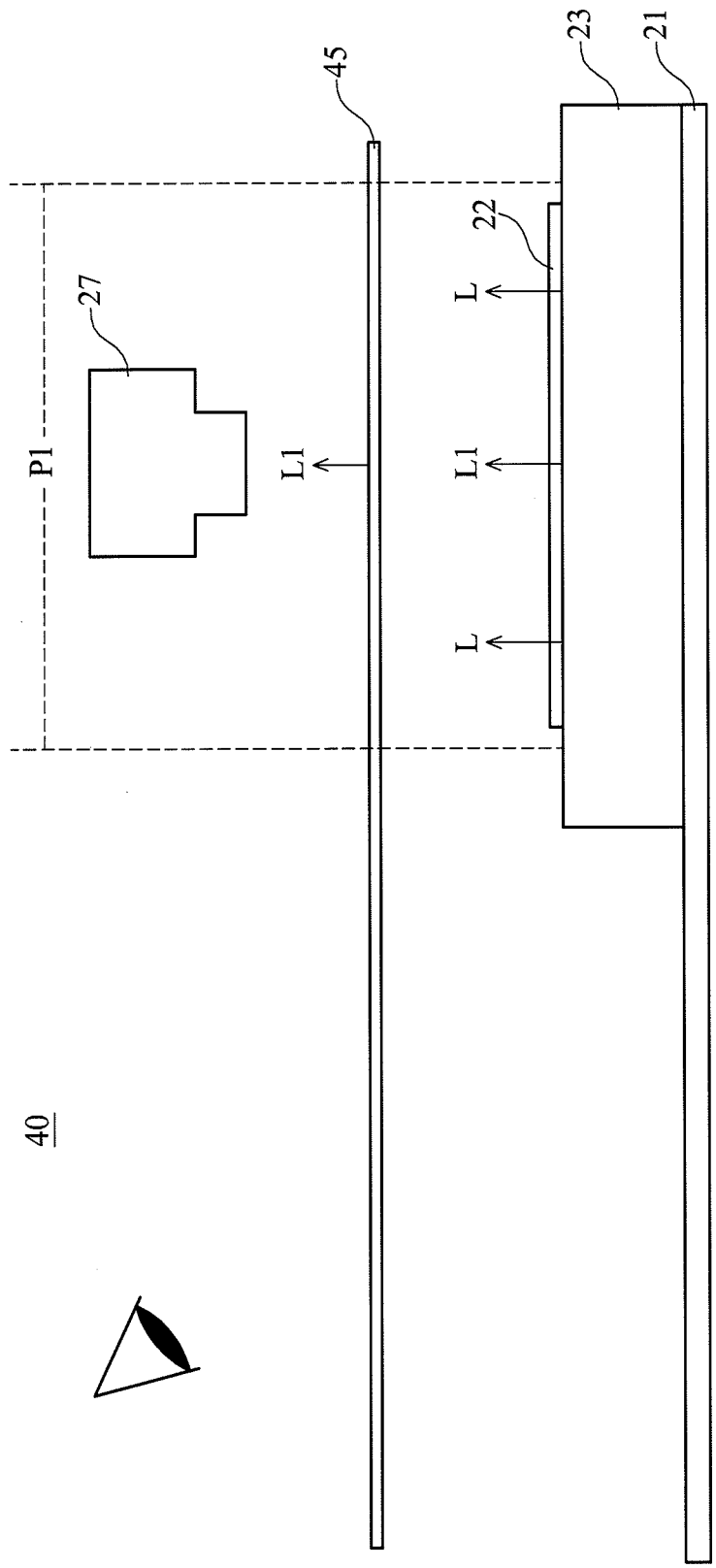
FIG. 5A is a schematic drawing showing the structure of a bio-sample image pickup device in accordance with a third embodiment of the present invention.
Figure 5B:
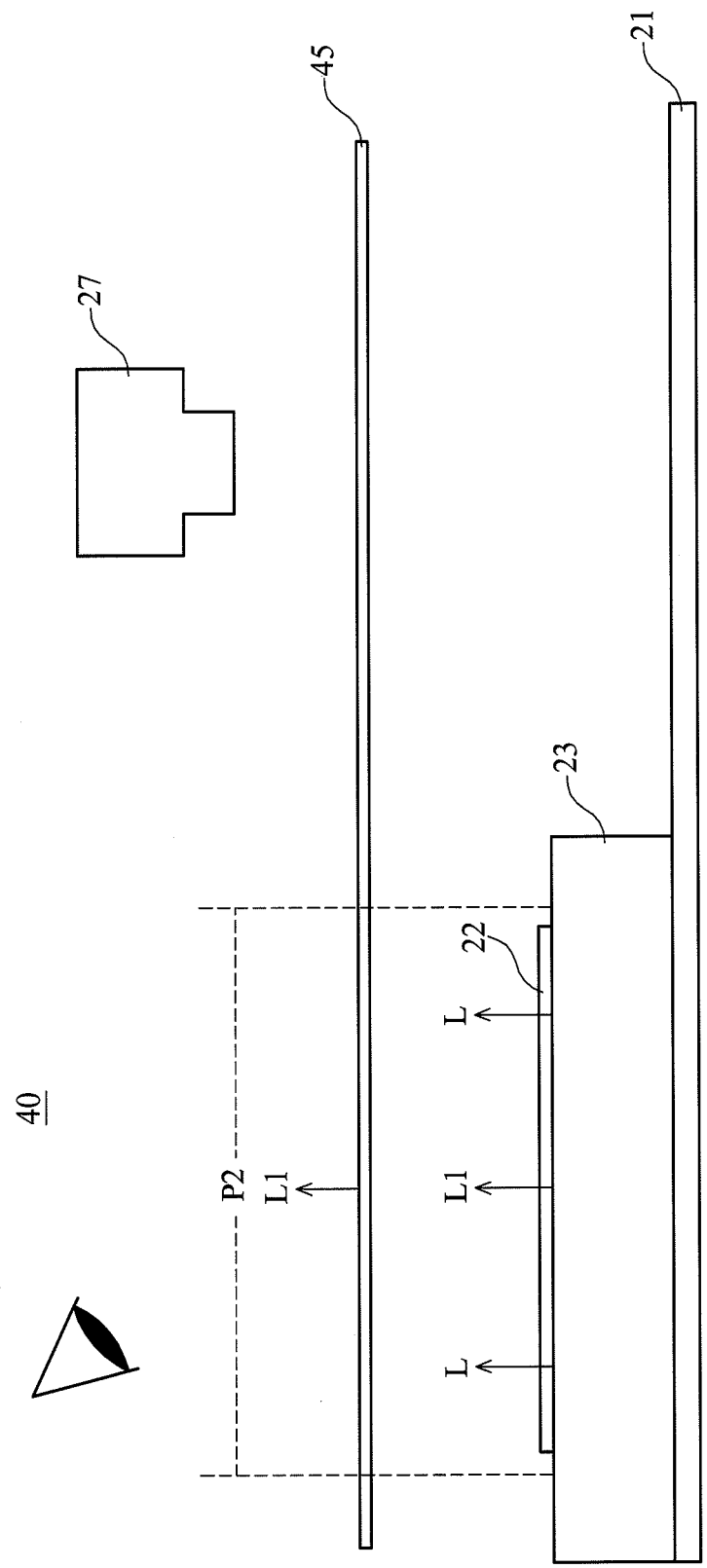
FIG. 5B corresponds to FIG. 5A, showing the bio-sample and the light source module moved to the second position.

FIG. 5A and FIG. 5B show a bio-sample image pickup device 40 in accordance with a third embodiment of the present invention. According to this third embodiment, the bio-sample image pickup device 40 comprises a carrier 21, a light source module 23, a filter 45 and an image pickup unit 27. When in use, a bio-sample 22 is placed on the light source module 23, allowing the image of the bio-sample 22 to be picked up by the image pickup unit 27.

The filter 45 extends from the first position P1 to the second position P2 so that a part of the filter 45 is disposed between the light source module 23 and the image pickup unit 27. When the light source module 23 is in the first position P1, the filter 45 filters the emitted light L and allows the first light L1 to pass therethrough toward the image pickup unit 27 so that the image pickup unit 27 can pick up the image of the bio-sample 22. When the light source module 23 is in the second position P2, the filter 45 filters the emitted light L and allows the first light L1 to pass therethrough, and therefore the operator can see the image of the bio-sample 22 that is formed of the first the first light L1.

According to this third embodiment, the filter 45 is set above the first position P1 and the second position P2, and adapted for filtering the emitted light L in the first position P1 and/or the second position P2. Therefore, the image pickup device 40 requires only one single filter 45 to filter the emitted light L in the first position P1 and the second position P2, allowing the image pickup unit 27 to pick up the image of the bio-sample 22 in the first position P1 and the operator to see the image of the bio-sample 22 in the second position P2.

Although particular embodiments of the invention have been described in detail for purposes of illustration, various modifications and enhancements may be made without departing from the spirit and scope of the invention. Accordingly, the invention is not to be limited except as by the appended claims.

What is claimed is:

1. A bio-sample image pickup device, comprising:
    a light source module adapted to emit light, allowing the emitted light to be projected onto a bio-sample;
    a carrier adapted to carry said light source module and said bio-sample, allowing said light source module and said bio-sample to be moved between a first position and a second position;
    an image pickup unit adapted to pick up the image of said bio-sample in said first position;
    a first filter set between said light source module and said image pickup unit and adapted to filter the light emitted by said light source module, wherein said image pickup unit picks up the image of said bio-sample in the first position via said first filter; and
    a second filter set in said second position and adapted to filter the light emitted by said light source module, allowing an operator to see the image of said bio-sample in said second position through said second filter.

2. The bio-sample image pickup device as claimed in claim 1, wherein said first filter is mounted on said image pickup unit.

3. The bio-sample image pickup device as claimed in claim 1, wherein said second filter is angularly adjustable.

4. The bio-sample image pickup device as claimed in claim 1, wherein said bio-sample is placed on said light source module so that a part of the light emitted by said light source module pass through said bio-sample and the other part of the light emitted by said light source module is converted by said bio-sample into a first light.

5. The bio-sample image pickup device as claimed in claim 1, wherein said bio-sample is a DNA gel obtained through gel electrophoresis.

6. A bio-sample image pickup device, comprising:
    a light source module adapted to emit light, allowing the emitted light to be projected onto a bio-sample;
    a carrier adapted to carry said light source module and said bio-sample, allowing said light source module and said bio-sample to be moved between a first position and a second position;
    an image pickup unit adapted to pick up the image of said bio-sample in said first position; and
    a filter mounted on said light source module and movable with said light source module between a first position and a second position and adapted to filter the light emitted by said light source module, wherein said image pickup unit adapts to pick up the image of said bio-sample in said first position via said filter and an operator is able to see the image of said bio-sample in said second position via said filter.

7. The bio-sample image pickup device as claimed in claim 6, wherein said bio-sample is placed on said light source module so that a part of the light emitted by said light source module pass through said bio-sample and the other part of the light emitted by said light source module is converted by said bio-sample into a first light.

8. The bio-sample image pickup device as claimed in claim 6, wherein said bio-sample is a DNA gel obtained through gel electrophoresis.

9. A bio-sample image pickup device, comprising:
    a light source module adapted to emit light, allowing the emitted light to be projected onto a bio-sample;
    a carrier adapted to carry said light source module and said bio-sample, allowing said light source module and said bio-sample to be moved between a first position and a second position;
    an image pickup unit adapted to pick up the image of said bio-sample in said first position; and
    a filter extending from said first position to said second position, wherein said image pickup unit adapts to pick up the image of said bio-sample in said first position via said filter and an operator is able to see the image of said bio-sample in said second position via said filter.

10. The bio-sample image pickup device as claimed in claim 9, wherein said bio-sample is placed on said light source module so that a part of the light emitted by said light source module pass through said bio-sample and the other part of the light emitted by said light source module is converted by said bio-sample into a first light.

* * * * *